(12) United States Patent
Isawa et al.

(10) Patent No.: US 8,277,860 B2
(45) Date of Patent: Oct. 2, 2012

(54) METHOD OF STABILIZING 1,4-DIHYDROXY-2-NAPHTHOIC ACID

(75) Inventors: Kakuhei Isawa, Odawara (JP); Tadashi Nakatsubo, Odawara (JP); Satoshi Hayashi, Odawara (JP); Yasushi Kubota, Odawara (JP)

(73) Assignee: Meiji Co., Ltd., Tokyo (JP)

( * ) Notice: Subject to any disclaimer, the term of this patent is extended or adjusted under 35 U.S.C. 154(b) by 1304 days.

(21) Appl. No.: 10/550,552

(22) PCT Filed: Mar. 26, 2004

(86) PCT No.: PCT/JP2004/004296
§ 371 (c)(1),
(2), (4) Date: Aug. 1, 2006

(87) PCT Pub. No.: WO2004/085364
PCT Pub. Date: Oct. 7, 2004

(65) Prior Publication Data
US 2006/0287553 A1    Dec. 21, 2006

(30) Foreign Application Priority Data
Mar. 26, 2003  (JP) .............................. P. 2003-084827

(51) Int. Cl.
*C11B 5/00* (2006.01)
*C07C 51/15* (2006.01)
*A21D 4/00* (2006.01)

(52) U.S. Cl. ......... 426/541; 426/321; 426/330; 562/425

(58) Field of Classification Search ................... 426/541
See application file for complete search history.

(56) References Cited

U.S. PATENT DOCUMENTS

| 2,104,415 A | * | 1/1938 | Davies ........................... 426/475 |
| 4,766,001 A | * | 8/1988 | Mizandjian et al. .......... 426/477 |

FOREIGN PATENT DOCUMENTS

| JP | 59-163128 A | 9/1984 |
| JP | 59-186942 A | 10/1984 |
| JP | 60-134823 A | 7/1985 |
| JP | 8-98677 A | 4/1996 |
| JP | 9-132545 A | 5/1997 |
| WO | WO 03/016544 A1 | 2/2003 |

OTHER PUBLICATIONS

Sukajang et al., Effects of sodium ascorbate and drying temperature on active protease of dried ginger. As J. Food Ag-Ind 2010, 3(01), 52-58.*
Translation of JP 58-163128, Sep. 1984.*
Communication issued by Japanese Patent Office on Mar. 9, 2010 in counterpart Japanese Application No. 2005-504118.
International Search Report Jul. 6, 2004.
Japanese Patent Office, Office Action issued Oct. 25, 2011 in corresponding Japanese Patent Application No. 2010-129989.

* cited by examiner

*Primary Examiner* — Humera Sheikh
*Assistant Examiner* — Lela S Williams
(74) *Attorney, Agent, or Firm* — Sughrue Mion, PLLC

(57) ABSTRACT

A method for stabilizing 1,4-dihydroxy-2-naphthoic acid, which comprises reducing an oxygen dissolved in a solution containing 1,4-dihydroxy-2-naphthoic acid, and food or drink containing 1,4-dihydroxy-2-naphthoic acid.

6 Claims, 2 Drawing Sheets

METHOD OF STABILIZING 1,4-DIHYDROXY-2-NAPHTHOIC ACID

TECHNICAL FIELD

The present invention relates to a method for stabilizing 1,4-dihydroxy-2-naphthoic acid (to be referred to as DHNA hereinafter) and food and drink comprising DHNA.

BACKGROUND OF THE INVENTION

It is known that DHNA is useful as an industrial material, for example, for dyestuffs, pigments, sensitive materials and the like, and various synthesizing methods thereof according to organic chemical syntheses have been reported (refer to, for example, JP-A-57-128655, JP-A-59-186942 and JP-A-60-104037). Since the aforementioned methods require a reaction in an organic solvent under high temperature and high pressure, or use of a reagent or the like which is not suitable for eating and drinking, as the catalyst or the like, DHNA obtained by such methods have not been employed in food and drink or pharmaceuticals.

Accordingly, the present inventors have carried out a study on an alternative method thereof, and found a method for producing DHNA in a large amount intracellularly and extracellularly by using the bacterium belonging to the genus *Propionibacterium*. Thereafter, it was found that the DHNA-containing composition obtained from this culture mixture, or DHNA or a salt thereof, is useful for the prevention, treatment and the like of metabolic bone disease, since it has the actions to improve intestinal flora and to reduce the abdominal discomfort symptom appeared in milk-sensitive patients at the time of milk ingestion, and further accelerates differentiation and functional expression of osteoblast and inhibits formation of osteoclast (refer to WO 03/016544 A1).

However, when a culture of the bacterium belonging to the genus *Propionibacterium* is applied to food and drink or pharmaceuticals as a food material for the purpose of adding the physiological function possessed by DHNA, there is a disadvantage that the residual amount of DHNA is considerably reduced during the production and storage thereof. For example, it is known that ascorbic acid, hyposulfurous acid and/or acetic anhydride is/are used for the stabilization of Bifidus factor contained in the culture mixture of the bacterium belonging to the genus *Propionibacterium* (refer to JP-A-10-108672). However, there are the outstanding problems in employing this method that the original taste of food and drink are impaired, or the substances cannot be used since they are not recognized as food additives, and the like.

DISCLOSURE OF THE INVENTION

The invention has been made by taking such technical situations into consideration and for the purpose of providing a new method as a method for stabilizing DHNA which has an excellent safety and can be employed without impairing the taste.

As a result of intensive studies carried out with the aim of achieving the aforementioned object, it is confirmed that DHNA is apt to be oxidized, and particularly, heat treatment in the presence of oxygen easily oxidizes DHNA and considerably reduces content thereof in a liquid. Accordingly, the inventors unexpectedly found that reduction of the DHNA content can be significantly inhibited without adding a stabilizing agent by reducing the dissolved oxygen in a liquid before heat-treating the liquid containing DHNA. The invention has been accomplished based on these new findings.

Accordingly, the invention relates to the following (1) to (10).

(1) A method for stabilizing 1,4-dihydroxy-2-naphthoic acid, which comprises reducing oxygen dissolved in a solution containing 1,4-dihydroxy-2-naphthoic acid.

(2) The method according to (1), which further comprises adding an antioxidant as a stabilizing agent of 1,4-dihydroxy-2-naphthoic acid.

(3) The method according to (1) or (2), which further comprises conducting a heat treatment to the solution containing 1,4-dihydroxy-2-naphthoic acid after reducing the oxygen dissolved in said solution.

(4) The method according to (3), wherein the oxygen dissolved in said solution is reduced during the heat treatment.

(5) The method according to (3), wherein the oxygen dissolved in said solution is reduced after the heat treatment.

(6) The method according to any one of (1) to (5), wherein the solution is at least one liquid food or drink selected from the group consisting of a milk, a drink containing a dairy product, a lactic acid bacteria beverage, a soy-milk, a vegetable juice, a fruit juice, a tea drink, a coffee drink, a cocoa drink, a sports drink, an energy drink, a carbonated beverage, an alcoholic beverage and a soup.

(7) The method according to any one of (1) to (6), wherein the solution is a solution containing a milk or a dairy product.

(8) The method according to any one of (1) to (7), wherein the oxygen dissolved in said solution is reduced by substituting with an inert gas.

(9) A method for producing food or drink containing 1,4-dihydroxy-2-naphthoic acid, which comprises stabilizing 1,4-dihydroxy-2-naphthoic acid by the method according to any one of (1) to (8).

(10) The method according to (9), wherein a part of or all of the process is carried out under conditions in which the oxygen is reduced.

(11) Food or drink produced by the method according to (9) or (10).

BEST MODE FOR CARRYING OUT THE INVENTION

Figure 1:
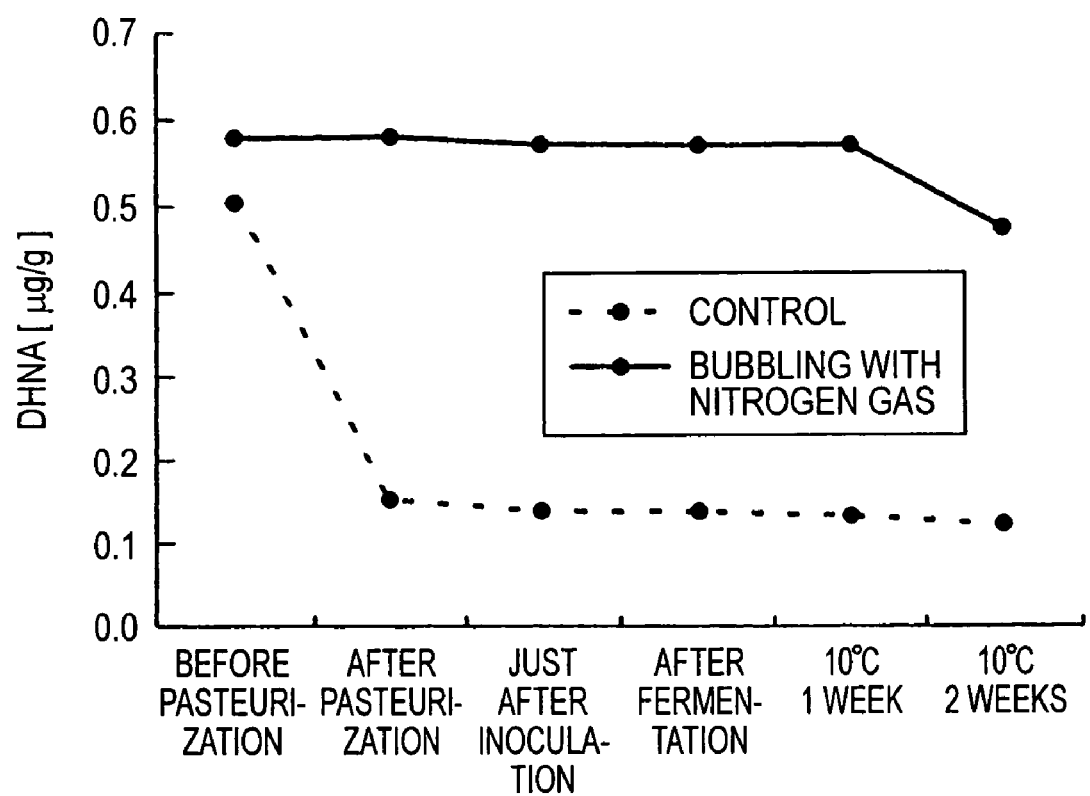
FIG. 1 is a graph showing the changes in the DHNA concentration during the preparation and preservation of a DHNA-containing plain yogurt.

The following describes the invention in detail.

In order to carry out the invention, it is necessary to reduce or eliminate the dissolved oxygen in the liquid. As the method, for example, inert gas such as nitrogen gas may be made into saturated state by bubbling the inert gas into the liquid to substitute the dissolved oxygen in the liquid therewith. Bubbling of the inert gas (hereinafter, the invention is described using nitrogen gas as the representative example) can be carried out in a tank and/or in a line. The temperature in the course of bubbling the inert gas is not particularly limited, so long as it is before the addition of DHNA. When the bubbling is carried out after the addition, it is desirable to carry out the bubbling at a temperature identical to or lower than that at the time of the addition of DHNA. In addition, the conventional method as a removing method of dissolved oxygen, such as the substitution of the air in a tank by nitrogen gas in advance or the charging of a liquid into a tank, followed by pressurization of its upper side through bubbling of nitrogen gas (JP-A-4-36178), can be applicable to the invention. Furthermore, it is desirable to carry out a part of or all steps of the production process under an atmosphere in which oxygen is cut off or reduced by substituting with the inert gas, so that the concentration of the dissolved oxygen in a solution can be kept at preferably 5 ppm or less, more preferably 2 ppm or less, and carried out in the same manner when the product is filled and packed.

In order to ensure the stability of DHNA in a solution, the concentration of the dissolved oxygen in the liquid is adjusted to preferably 5 ppm or less, and more preferably 2 ppm or less. Lower limit of the concentration of the dissolved oxygen in the liquid is not particularly limited, but is preferably 0 ppm or more.

When a DHNA-containing liquid is prepared by adding a DHNA-containing composition or DHNA or a salt thereof to a solution to be used as the base (refer to WO 03/016544 A1), it is desirable to carry out the addition under such a condition that the dissolved oxygen in the base solution is removed by nitrogen substitution, and production example of the DHNA containing composition is described in the aforementioned patent reference WO 03/016544 A1. Specifically, the DHNA-containing composition can be obtained by inoculating and culturing *Propionibacterium freudenreichii* in a medium prepared, for example, by adding beer yeast extract to skim milk powder or a proteolysis-treated product of skim milk powder. The amount of DHNA to be added is optionally increased or decreased according to the use and form and is not particularly limited, but the upper limit thereof is preferably 1 mg/ml or less, and more preferably 500 μg/ml or less, and the lower limit thereof is preferably larger than 0 μg/ml, and more preferably 0.01 μg/ml or more. When the object is the improvement of the abdominal discomfort symptom, as an example, DHNA is added in such an amount that the content thereof per 100 ml of final product becomes about 11 μg (refer to WO 03/016544 A1). In this case, the amount to be added can be accordingly adjusted with taking heat pasteurization conditions and preservation conditions into consideration. The temperature at the time of adding DHNA is 90° C. or less, preferably 45 to 40° C. or less, and more preferably about 10° C. When the amount of the dissolved oxygen in a liquid is reduced after the addition of DHNA, the lower temperature is more preferable. Although the lower limit of the temperature at the time of adding DHNA is not particularly limited, it is preferably 0° C. or more.

The substitution time with nitrogen gas is not particularly limited, and it can be carried out at any step of the production process. However, since the residual amount of DHNA in a liquid is most apt to be influenced by heating, it is most effective according to the invention to reduce the dissolved oxygen before heating of the DHNA-containing liquid, particularly before the heat pasteurization treatment.

During the heat pasteurization treatment, in the case of milk for example, the treatment is established by the Ministerial Ordinance concerning compositional standards, etc. for Milk and Milk Products, and generally, there are low-temperature long time pasteurization, high-temperature long time pasteurization, high-temperature short time pasteurization, ultra high-temperature flash pasteurization and the like pasteurization methods. According to the invention, any of the pasteurization methods and sterilization methods including the above can be used, and both of the batch system and continuous system can be applicable. Although the treating temperature and treating time vary depending on the pasteurization method, they are selected preferably within the range of from 50° C. to 200° C. and from 0.1 second to 1 hour according to the aforementioned pasteurization method. Including the former, when the DHNA-containing liquid has a frequent chance to be brought into contact with oxygen during the heat pasteurization, it is desirable to keep the amount of the dissolved oxygen in the liquid to be decreased. Accordingly, it is desirable to carry out the substitution with nitrogen gas continuously even during the heat pasteurization.

As the inert gas, nitrogen gas, argon gas, carbon dioxide gas and the like can be specifically mentioned. Among all, nitrogen gas is preferably used, since the nitrogen gas is present in the air in a large quantity and the cost thereof is relatively low, and what is more, the safety thereof is confirmed and it does not exert influence on the taste and quality of food and drink.

Also, addition of an antioxidant to the intended solution is also useful for the stabilization of DHNA. As the adding time of antioxidant, it is preferable to be added before the addition of DHNA. Examples of the antioxidant include hyposulfurous acid, ascorbic acid, erythorbic acid, carotene, tocopherol and polyphenols having antioxidant action, examples of the polyphenols include synthesized products as well as natural products such as teas, a grape, a lemon, coffee, a purple-fleshed sweet potato, a soybean and the like, and in addition to the squeezed juices of fruits, vegetables, seeds, plant leaves and the like which are rich in these polyphenols, extracts thereof with water or an organic solvent may be used, or their concentrated products, purified products or dried products may also be used. Regarding the amount of the antioxidant to be added, an amount equivalent to or larger than the adding amount generally used for the purpose of anti-oxidation may be added according to the kind of antioxidant. For example, when ascorbic acid is added solely without carrying out bubbling with the inert gas, it is desirable to add in an amount of 0.01% by weight or more based on the total weight of the solution.

The object matter to which the invention can be applied is not particularly limited, so long as it is a liquid substance when the dissolved oxygen is reduced. For example, the solution may be any food which can be taken for drinking use, including milk; a drink containing a dairy product; a lactic acid bacteria beverage; a soy-milk; a vegetable juice; a fruit juice (including drinks that contain them); a tea system drink such as green tea, black tea, oolong tea or the like; a coffee drink; a cocoa drink; a sports drink which contains amino acids, vitamins and the like and is particularly suited for water supplement and nutrition supplement at the rime of practicing sports; a energy drink having a reinforced nutrient components for the purpose of improving health; a carbonated beverage or the like soft drink; an alcoholic beverage; and soup, miso soup, clear soup and the like soups, and it can finally take not only a liquid shape but also any one of fluid shape, paste shape, gel shape, powder shape, granular shape, tablet shape and solid shape. Specifically, those in which the aforementioned foods and drinks are processed into jelly shape, gel shape, freeze-dried shape and the like or into such a shape that they are covered with a starchy viscous layer; dairy products such as yogurt, cheese, cream, butter, ice cream, modified milk powder and the like; pastes such as spread, jam and the like, desserts such as jelly, pudding, Bavarian cream and the like; seasonings such as mayonnaise, dressing and the like; and liquid diets and the like can be mentioned. The invention can be applied not only to these foods but also to healthy foods, and foods for specified health use, foods with health claims and the like physiologically functional foods are included in this healthy foods. In addition, since DHNA is excellent in solubility and stability in organic solvents, the invention can also be applied to the production of pharmaceuticals having an excellent safety.

In general, DHNA is ingested in a daily amount of preferably from 0.03 to 3 μg, more preferably from 0.1 to 1 μg, per 1 kg of human or animal.

In addition, it is desirable to keep the state of reduced dissolved oxygen even in the case of the final product containing DHNA. For the benefit of preservation, a plastic material such as polyvinyl chloride alcohol, a metallic foil or the like having a high gas-barrier property may be used solely, or a container or package laminated therewith may be used according to the necessity. In addition, a container or a package having high a shading property may also be used.

Although the following describes the invention in more detail with reference to examples, the invention is not limited to the followings.

EXAMPLE 1

Determination Method of DHNA

A 5 ml portion of each sample was passed through a solid phase extraction column (Oasis HLB, manufactured by Waters Corporation) conditioned with 5 ml of methanol and 4 ml of 1% (w/v) sodium ascorbate aqueous solution. After washing with 5 ml of an aqueous solution of 1% (w/v) sodium ascorbate and elution with 4 ml of an aqueous solution of 10% (w/v) sodium ascorbate/methanol (1:9), the thus obtained eluate was concentrated under reduced pressure. A 1 ml portion thereof was sampled and filled up with the aforementioned sodium ascorbate-containing methanol. The mixture was filtered through a 0.5 μm filter and subjected to HPLC (column: Cadenza CD-C18 (4.6×150 mm, manufactured by Imtact Corporation), mobile phase: acetonitrile, methanol, water and acetic acid (10:20:200:0.1, vol/vol/vol/vol, adjusted to pH 7 with aqueous ammonia), detector: UV detector, detection wavelength: 254 nm, flow rate: 1.5 ml/min, column temperature: 45° C., sample injection: 20 μl). A calibration curve was prepared by preparing a 1 mg/ml (methanol solution) standard stock solution of a DHNA preparation (046-22422, manufactured by Wako Pure Chemical Industries, Ltd.) and using the solution after optionally diluting with methanol.

EXAMPLE 2

Production Method of DHNA-containing Plain Yogurt and Nitrogen Gas Substitution Test In order to prepare a plain yogurt to which a DHNA-containing composition was added, bulk starters were firstly prepared by respectively inoculating 1% by weight of $L.$ $bulgaricus$ JCM 1002T and $S.$ $thermophilus$ ATCC 19258 into a 10% by weight skim milk powder medium and culturing them at 37° C. for 15 hours. The raw materials excluding the DHNA-containing composition, namely 80% by weight of commercial milk, 2% by weight of skim milk powder and 14.5% by weight of water, were mixed while bubbling with nitrogen gas. Dissolved oxygen concentration of the mix was about 10 ppm before the bubbling, but reduced to less than 1 ppm by the bubbling with nitrogen gas. The DHNA-containing composition (the DHNA content of 40 μg/ml) prepared in accordance with the Example 2 of WO 03/016544 A1 was added in an amount of 1.5% by weight to the mix, pasteurized by heating at 95° C. for 5 minutes by a batch system and then cooled to 43° C. After each of the aforementioned bulk starters was inoculated therein in an amount of 1% by weight, and then aseptically filled and sealed in a sterilized non-barrier polystyrene container (manufactured by Asahi Plastics Co., Ltd.). In this connection, the bubbling of nitrogen was continued until inoculation of the starters and, after the filling, the fermentation was carried out at 43° C. for 4 hours. After completion of the fermentation, cooling was carried out at 5° C., and preservation of the thus obtained DHNA-containing plain yogurt was carried out in the dark place at 10° C. for 2 weeks. The case in which the bubbling with nitrogen gas was not carried out during the preparation of plain yogurt was used as the control.

The DHNA content contained in the plain yogurt was measured in accordance with the aforementioned test example, at respective steps of before pasteurization of the mix, after pasteurization of the same, just after inoculation of the bulk starter and completion of the fermentation, and after the lapse of the preservation for 1 week and 2 weeks, according to the production of plain yogurt of this Example. The results are shown in FIG. 1. AS is evident from the figure, the loss of DHNA during the preparation and preservation is almost completely inhibited by bubbling the mix with nitrogen gas during the preparation of plain yogurt. On the other hand, it is found that the DHNA content in the control is reduced to about 30% by the heat pasteurization process, in comparison with the content before heat pasteurization.

EXAMPLE 3

Production Method of DHNA-Containing Vegetable Drink and Nitrogen Gas Substitution Test In order to prepare a vegetable drink to which a DHNA-containing composition was added, firstly, 200 kg of a concentrated carrot juice Bx42, 20 kg of a concentrated tomato juice Bx60GY, 36 kg of a vegetable mix juice (all manufactured by Sanyo Foods) and 280 kg of a transparent apple juice Bx70 (manufactured by Mitsubishi Corporation) were weighed and then mixed, and 6 kg of ascorbic acid and 4 kg of a lemon perfume (manufactured by SHONAN FLAVORS, INC.) were added thereto, and subsequently water was added to be adjusted to 4 t. A vegetable drink to which a DHNA-containing composition was added was prepared by adding 0.2% by weight or 0.4% by weight of the DHNA-containing composition prepared in accordance with Example 2 of WO 03/016544 A1 (the DHNA content of 58 μg/ml, with the proviso that the halfway addition of lactose was not carried out but the nitrogen gas bubbling was changed to aeration in the middle of the culturing) to this mixture at 10° C.

Figure 2:
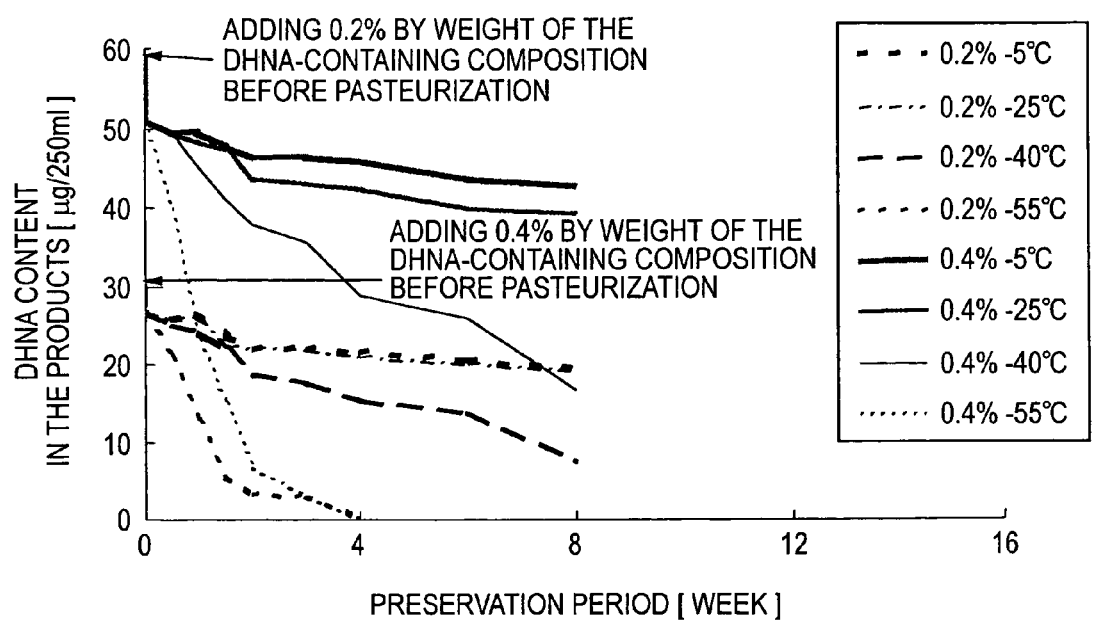
FIG. 2 is a graph showing the changes in the DHNA concentration during the preservation of a DHNA-containing vegetable drink.

Just before the heating of this mixture by a plate, nitrogen was bubbled at a flow rate of 50.0 l/min at 10° C. until the dissolved oxygen became 5 ppm. Thereafter, the mixture was pasteurized at 140° C. for 3 seconds, and the mixture homogenized to 250 kg/cm$^2$ was cooled to 25° C. and aseptically filled in Tetra Brick-Aseptic (manufactured by Tetra Pack). The thus obtained vegetable drink to which the DHNA-containing composition was added was preserved at 5, 25, 30, 40 or 55° C. for 2 months. The DHNA content (μg/250 ml) in the vegetable drink is shown in FIG. 2. As a result, it is confirmed that reduction of the DHNA content can be inhibited for a prolonged period of time even by the ordinary temperature (25° C.) preservation.

Industrial Applicability

By the invention, it becomes possible for the first time to significantly inhibit the reduction of the DHNA content through the reduction of liquid dissolved oxygen, without impairing the original tastes of food and drink.

The invention claimed is:

1. A method for stabilizing 1,4-dihydroxy-2naphthoic acid, which comprises reducing the level of oxygen dissolved in a solution containing the 1,4-dihydroxy-2-naphthoic acid to 5 ppm or less, by substituting the oxygen with an inert gas without adding a stabilizing agent, and further conducting a heat treatment on the solution wherein the solution is at least one liquid food or drink selected from the group consisting of a milk, a drink containing a dairy product, a lactic acid bacteria beverage, a soy-milk, a vegetable juice, a fruit juice, a tea drink, a coffee drink, a cocoa drink, a sports drink, an energy drink, a carbonated beverage, an alcoholic beverage and a soup.

2. A method for producing liquid food or drink containing 1,4-dihydroxy-2-naphthoic acid, which comprises stabilizing 1,4-dihydroxy-2-naphthoic acid by reducing the level of oxygen dissolved in a soulution containing the 1,4-dihydroxy-2-naphthoic acid to 5 ppm or less by substituting the oxygen with an inert gas without adding a stabilizing agent, and further conducting a heat treatment on the solution wherein the solution is at least one liquid food or drink selected from the group consisting of a milk, a drink containing a dairy product, a lactic acid bacteria beverage, a soy-milk, a vegetable juice, a fruit juice, a tea drink, a coffee drink, a cocoa drink, a sports drink, an energy drink, a carbonated beverage, an alcoholic beverage and a soup.

3. The method according to claim 1 or 2, wherein the oxygen dissolved in said solution is kept reduced during the heat treatment.

4. The method according to claim 1 or 2, wherein the oxygen dissolved in said solution is kept reduced after the heat treatment.

5. The method according to claims 1 or 2, wherein the solution is a solution containing a milk or a dairy product.

6. The method according to claim 2, which is carried out partially or entirely under conditions in which the oxygen is reduced.

* * * * *

UNITED STATES PATENT AND TRADEMARK OFFICE
CERTIFICATE OF CORRECTION

PATENT NO.       : 8,277,860 B2                         Page 1 of 1
APPLICATION NO.  : 10/550552
DATED            : October 2, 2012
INVENTOR(S)      : Kakuhei Isawa et al.

It is certified that error appears in the above-identified patent and that said Letters Patent is hereby corrected as shown below:

Title Page item (54) and col. 1, line 1, should read:

METHOD ~~OF~~ FOR STABILIZING
1,4-DIHYDROXY-2-NAPHTHOIC ACID

Signed and Sealed this
Thirteenth Day of November, 2012

David J. Kappos
*Director of the United States Patent and Trademark Office*